United States Patent
Giorgetti

(10) Patent No.: US 11,452,702 B2
(45) Date of Patent: *Sep. 27, 2022

(54) COMPOSITIONS COMPRISING AMINO ACIDS FOR USE IN THE TREATMENT OF MITOCHONDRIAL DYSFUNCTION-RELATED DISEASES

(71) Applicant: PROFESSIONAL DIETETICS INTERNATIONAL S.R.L., Milan (IT)

(72) Inventor: Paolo Luca Maria Giorgetti, Milan (IT)

(73) Assignee: Professional Dietetics International S.R.L., Milan (IT)

( * ) Notice: Subject to any disclaimer, the term of this patent is extended or adjusted under 35 U.S.C. 154(b) by 130 days.

This patent is subject to a terminal disclaimer.

(21) Appl. No.: 16/634,424

(22) PCT Filed: Jul. 20, 2018

(86) PCT No.: PCT/IB2018/055428
§ 371 (c)(1),
(2) Date: Jan. 27, 2020

(87) PCT Pub. No.: WO2019/021137
PCT Pub. Date: Jan. 31, 2019

(65) Prior Publication Data
US 2020/0253906 A1    Aug. 13, 2020

(30) Foreign Application Priority Data
Jul. 28, 2017    (IT) ........................ 102017000087376

(51) Int. Cl.
| *A61K 31/198* | (2006.01) |
| *A61P 3/04* | (2006.01) |
| *A61K 31/194* | (2006.01) |
| *A61K 31/405* | (2006.01) |
| *A61K 31/4172* | (2006.01) |
| *A61K 31/4415* | (2006.01) |
| *A61K 31/51* | (2006.01) |

(52) U.S. Cl.
CPC .......... *A61K 31/198* (2013.01); *A61K 31/194* (2013.01); *A61K 31/405* (2013.01); *A61K 31/4172* (2013.01); *A61K 31/4415* (2013.01); *A61K 31/51* (2013.01); *A61P 3/04* (2018.01)

(58) Field of Classification Search
CPC .................................................. A61K 31/198
USPC .......................................................... 514/89
See application file for complete search history.

(56) References Cited

U.S. PATENT DOCUMENTS

2003/0013761 A1   1/2003   Joshi et al.
2013/0237605 A1   9/2013   Zemel et al.
2014/0315788 A1  10/2014   Wolfe et al.
2020/0230093 A1   7/2020   Giorgetti
2021/0260011 A1   8/2021   Giorgetti

FOREIGN PATENT DOCUMENTS

| CA | 2972889 A1 | 9/2016 |
| EP | 2196203 B1 | 8/2012 |
| JP | 2005501068 A | 1/2005 |
| JP | 2018515441 A | 6/2018 |
| JP | 2018520204 A | 7/2018 |
| WO | 0151047 A1 | 7/2001 |
| WO | 2005034932 A2 | 4/2005 |
| WO | 2016093104 A | 6/2016 |
| WO | 2016/179657 | 11/2016 |
| WO | 2016181335 A1 | 11/2016 |
| WO | 2017/020121 | 2/2017 |
| WO | 2017/089612 | 6/2017 |

OTHER PUBLICATIONS

International Search Report for PCT/IB2018/055428, dated Nov. 6, 2018, 5 pages.
Written Opinion of the ISA for PCT/IB2018/055428, dated Nov. 6, 2018, 7 pages.
International Search Report and Written Opinion of the ISA for PCT/IB2019/052694 dated Jun. 25, 2019, 11 pages.
Database WPI Week 200744, May 3, 2007, Thomson Scientific, London, GB, XP002788927, 3 pages.
Restriction Requirement mailed in U.S. Appl. No. 16/634,330 dated May 6, 2021.
Nakagaichi, M., et al., "Effects of Exercise Training Plus Vespa Amino Acid Mixture (VAAM) Ingestion in Obese Women," Japanese Journal of Health Promotion, 3, 11-16, 2001 with English Abstract.
Nakamura, E., et al., "Assessment of Biological Age by Principal Component Analysis," Mechanisms of Ageing and Development, vol. 46. Issues1-3, pp. 1-18, 1988, with English Translation of Office Action for JP Application No. 2019-566744 citing Nakamura attached to satisfy the requirement for a concise explanation of relevance.
Brocca, L., et al., "Proteomic analysis of plasma after branched chain enriched mixture supplementation in mice", Journal of the International Society of Sports Nutrition, vol. 10, No. 1, Apr. 3, 2013, 5 pages.
International Search Report and Written Opinion of the ISA for PCT/IB2018/055425 dated Nov. 2, 2018, 17 pages.
Bournat, J.C., et al., Mitochondrial Dysfunction in Obesity Current Opinion Endocrinol Obesity, Oct. 17, 2010 (5): 446-452.

(Continued)

*Primary Examiner* — Nizal S Chandrakumar
(74) *Attorney, Agent, or Firm* — Nixon & Vanderhye, PC

(57) ABSTRACT

Composition for promoting mitochondrial biogenesis and improving mitochondrial function in a subject, the composition comprising an active agent, said active agent containing the amino acids leucine, isoleucine, valine, threonine, lysine and citric acid, succinic acid, malic acid.

17 Claims, 6 Drawing Sheets

Specification includes a Sequence Listing.

(56) References Cited

OTHER PUBLICATIONS

Gorshinova et al., "Mitochondrial dysfunction as one of the mechanisms of impaired reproductive function in obesity." Akusherstvo i ginekologiya/Obstetrics and Gynecology. 2014; 7: 9-13. in Russian with English Abstract.

Non-Final Office Action issued in co-pending U.S. Appl. No. 16/634,330, dated Jun. 30, 2021.

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: GAPDH Primer sense 5'-3'

<400> SEQUENCE: 1
aactttggca ttgtggaagg                                          20

<210> SEQ ID NO 2
<211> LENGTH: 20
<212> TYPE: DNA
<213> ORGANISM: Artificial Sequence
<220> FEATURE:
<223> OTHER INFORMATION: GAPDH Primer Antisense 5'-3'

<400> SEQUENCE: 2
```

```
acacattggg ggtaggaaca                                              20

<210> SEQ ID NO 3
<211> LENGTH: 22
<212> TYPE: DNA
<213> ORGANISM: Artificial Sequence
<220> FEATURE:
<223> OTHER INFORMATION: Primer Cyt c Sense 5'-3'

<400> SEQUENCE: 3 atagggcat gtcacctcaa ac                                            22

<210> SEQ ID NO 4
<211> LENGTH: 22
<212> TYPE: DNA
<213> ORGANISM: Artificial Sequence
<220> FEATURE:
<223> OTHER INFORMATION: Primer Cyt c Antisense 5'-3'

<400> SEQUENCE: 4
gtggttagcc atgacctgaa ag                                           22

<210> SEQ ID NO 5
<211> LENGTH: 24
<212> TYPE: DNA
<213> ORGANISM: Artificial Sequence
<220> FEATURE:
<223> OTHER INFORMATION: Primer PGC-1a Sense 5'-3'

<400> SEQUENCE: 5
actatgaatc aagccactac agac                                         24

<210> SEQ ID NO 6
<211> LENGTH: 22
<212> TYPE: DNA
<213> ORGANISM: Artificial Sequence
<220> FEATURE:
<223> OTHER INFORMATION: Primer PGC-1a Antisense 5'-3'

<400> SEQUENCE: 6
ttcatccctc ttgagccttt cg                                           22

<210> SEQ ID NO 7
<211> LENGTH: 25
<212> TYPE: DNA
<213> ORGANISM: Artificial Sequence
<220> FEATURE:
<223> OTHER INFORMATION: Primer Tfam Sense 5'-3'

<400> SEQUENCE: 7
aagacctcgt tcagcatata acatt                                        25

<210> SEQ ID NO 8
<211> LENGTH: 23
<212> TYPE: DNA
<213> ORGANISM: Artificial Sequence
<220> FEATURE:
<223> OTHER INFORMATION: Primer Tfam Antisense 5'-3'

<400> SEQUENCE: 8
ttttccaagc ctcatttaca agc                                          23

<210> SEQ ID NO 9
<211> LENGTH: 21
<212> TYPE: DNA
```

```
<213> ORGANISM: Artificial Sequence
<220> FEATURE:
<223> OTHER INFORMATION: Primer KFL15 Sense 5'-3'

<400> SEQUENCE: 9
acaccaagag cagccacctc a                                              21

<210> SEQ ID NO 10
<211> LENGTH: 20
<212> TYPE: DNA
<213> ORGANISM: Artificial Sequence
<220> FEATURE:
<223> OTHER INFORMATION: Primer KFL15 Antisense 5'-3'

<400> SEQUENCE: 10
tgagatcgcc ggtgccttga                                                20

<210> SEQ ID NO 11
<211> LENGTH: 18
<212> TYPE: DNA
<213> ORGANISM: Artificial Sequence
<220> FEATURE:
<223> OTHER INFORMATION: Primer PP2CM Sense 5'-3'

<400> SEQUENCE: 11
accacaggca ggcgactc                                                  18

<210> SEQ ID NO 12
<211> LENGTH: 22
<212> TYPE: DNA
<213> ORGANISM: Artificial Sequence
<220> FEATURE:
<223> OTHER INFORMATION: Primer PP2CM Antisense 5'-3'

<400> SEQUENCE: 12
tggctcatca atgcggttat cc                                             22

<210> SEQ ID NO 13
<211> LENGTH: 23
<212> TYPE: DNA
<213> ORGANISM: Artificial Sequence
<220> FEATURE:
<223> OTHER INFORMATION: Primer mtDNA Sense 5'-3'

<400> SEQUENCE: 13
acatgcaaac ctccatagac cgg                                            23

<210> SEQ ID NO 14
<211> LENGTH: 20
<212> TYPE: DNA
<213> ORGANISM: Artificial Sequence
<220> FEATURE:
<223> OTHER INFORMATION: Primer mtDNA Antisense 5'-3'

<400> SEQUENCE: 14
tcactgctga gtcccgtggg                                                20

<210> SEQ ID NO 15
<211> LENGTH: 20
<212> TYPE: DNA
<213> ORGANISM: Artificial Sequence
<220> FEATURE:
<223> OTHER INFORMATION: Primer gDNA Sense 5'-3'

<400> SEQUENCE: 15
ggtcgcggtg tgggcatttg                                                20
```

```
<210> SEQ ID NO 16
<211> LENGTH: 20
<212> TYPE: DNA
<213> ORGANISM: Artificial Sequence
<220> FEATURE:
<223> OTHER INFORMATION: Primer gDNA Antisense 5'-3'

<400> SEQUENCE: 16
cgtgatcgta gcgtctggtt                                              20
```

COMPOSITIONS COMPRISING AMINO ACIDS FOR USE IN THE TREATMENT OF MITOCHONDRIAL DYSFUNCTION-RELATED DISEASES

This application is the U.S. national phase of International Application No. PCT/IB2018/055428 filed 20 Jul. 2018, which designated the U.S. and claims priority to IT Patent Application No. 102017000087376 filed 28 Jul. 2017, the entire contents of each of which are hereby incorporated by reference.

FIELD OF THE INVENTION

The present description relates generally to compositions comprising amino acids. More particularly, the description relates to compositions comprising amino acids for use in medicine, in particular for use in the treatment of diseases related to mitochondrial dysfunction.

BACKGROUND

Mitochondria are cellular organelles which primary function is oxidative phosphorylation, a process through which energy derived from metabolism of glucose or fatty acids is converted to adenosine triphosphate (ATP). ATP is then used to drive various energy-requiring biosynthetic reactions and other metabolic activities.

Mitochondrial dysfunction may affect any tissue with a resulting large variety of symptoms, depending on the extent to which the different tissues are involved.

Diseases arising from mitochondrial dysfunction may include for example, mitochondrial swelling due to mitochondrial membrane potential malfunction, functional disorders due to oxidative stress such as by the action of reactive oxygen species (ROS) or free radicals, functional disorders due to genetic mutations and diseases due to functional deficiency of oxidative phosphorylation mechanisms for energy production.

Mitochondria deteriorate with age, losing respiratory activity, accumulating damage to their DNA (mtDNA) and producing excessive amounts of reactive oxygen species (ROS).

Recent evidence points to involvement of mitochondrial dysfunction in several diseases, including the age-related metabolic and cardiovascular disorders (atherosclerosis), in addition to the major neurodegenerative diseases such as Alzheimer's disease, Parkinson's disease and Huntington's disease and to chronic obstructive pulmonary disease (COPD).

Mitochondrial dysfunction has also been found in obesity and related disorders, including type 2 diabetes mellitus, high blood pressure, dyslipidemia, heart failure, kidney disease and osteoporosis.

Notably, sarcopenia, defined as one of the most important causes of functional decline and loss of independence in older adults due to involuntary loss of skeletal muscle mass and strength, and key feature of the so-called frailty syndrome, is due to reduced mitochondrial mass and function. Other muscle wasting diseases and disorder are known, including, for example, cachexia. Cachexia or wasting syndrome is defined as an unintentional loss of body weight, muscle atrophy, fatigue, and weakness. Cachexia is seen in people with cancer, AIDS, coeliac disease, COPD, multiple sclerosis, rheumatoid arthritis, congestive heart failure, tuberculosis and anorexia nervosa. No drugs or nutrients have been found to prevent and/or treat this condition.

Thus, given the worldwide obesity epidemics and increasing population ageing, the most frequent patients in the next future will be sarcopenic, obese elderly subjects.

Obesity and its associated diseases, such as insulin resistance and type 2 diabetes, are nowadays a major health problem, with more than 1.4 billion overweight adults (World Health Organization. Obesity and overweight. WHO Media Centre). Among them, ~500 million are obese and 40 million children under the age of 5 are currently classified as overweight or obese (World Health Organization. Obesity and overweight. WHO Media Centre).

From a metabolic point of view, obesity takes place when energy intake exceeds energy expenditure (EE) consequent to decreased mitochondrial function; therefore, besides dietary interventions aimed to decrease energy intake, another approach is to increase energy expenditure by means, for example, of physical exercise. However, this is not a simple task, especially for obese individuals, which often show obesity-associated muscle dysfunction (Wells et al., 2008).

Therefore, there is a growing need for new therapeutic approaches aimed to achieve weight loss and reduce the social and medical impact of this disease.

SUMMARY OF THE INVENTION

The present description has the aim of providing new amino acid based compositions particularly effective in increasing mitochondrial function and thus in the treatment of the obesity and related disorders.

According to the present description, the above object is achieved thanks to the subject matter specifically recalled in the ensuing claims, which are understood as forming an integral part of this disclosure.

An embodiment of the present description provides a composition for promoting mitochondrial biogenesis and improving mitochondrial function in a subject, the composition comprising an active agent, said active agent containing the amino acids leucine, isoleucine, valine, threonine, lysine and citric acid, succinic acid, malic acid.

In one or more embodiments, the active agent of the composition further contains one or more amino acids selected in the group consisting of histidine, phenylalanine, methionine, tryptophan, cysteine and tyrosine.

In one or more embodiments, the compositions herein disclosed may be used in medicine.

In a preferred embodiment, the compositions may be used in the treatment and/or prevention of a mitochondrial dysfunction-related disease, wherein said disease is obesity.

BRIEF DESCRIPTION OF THE DRAWINGS

The invention will now be described, by way of example only, with reference to the enclosed figures, wherein.

DETAILED DESCRIPTION OF PREFERRED EMBODIMENTS

Figure 1:
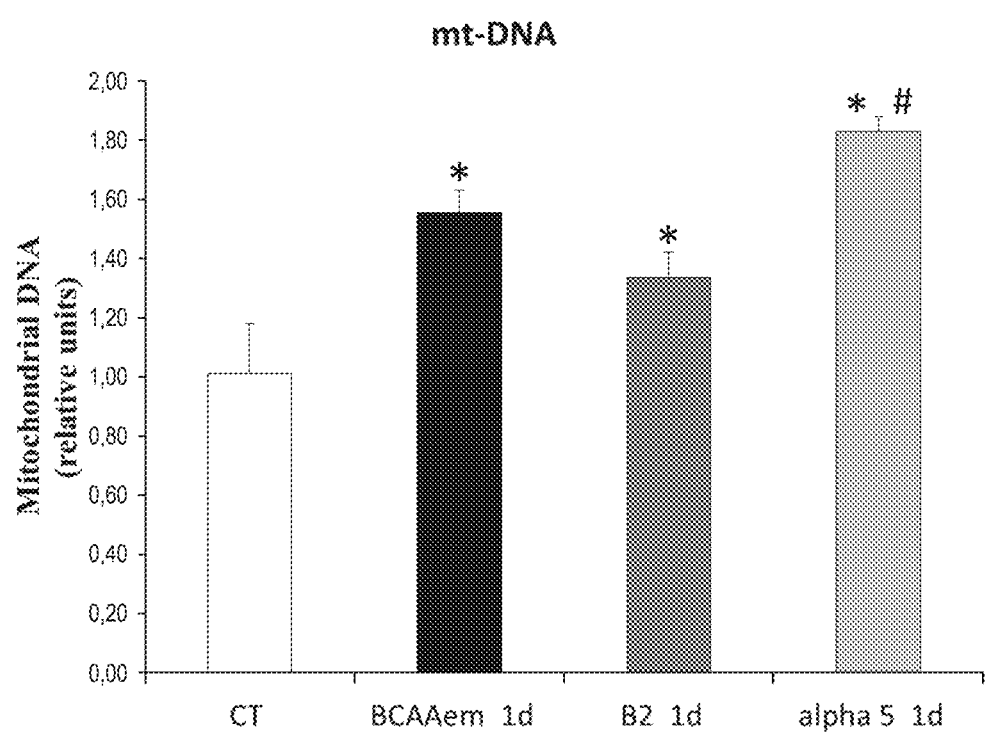
FIG. 1 shows the content of mitochondrial DNA (mtDNA) analysed by means of quantitative PCR in HL-1 cardiomyocytes treated with different amino acid based compositions for 48 hours (48 hr, 2 d). The quantitative PCR is performed in triplicate and normalized to genomic-DNA coding for the GAPDH (n=3, mean±SEM). Value of untreated cells (CT) is taken as 1.0 (*p<0.05 vs. untreated cells, #p<0.05 vs. BCAAem and B2).

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

In one or more embodiments, the composition herein disclosed comprises an active agent, the active agent containing the amino acids leucine, isoleucine, valine, threonine, lysine and the acids citric acid, succinic acid, malic acid.

A composition comprising amino acids—as disclosed in EP 2 196 203 B1—was administrated in mammals as alternative solution to provide benefits of calory restriction (CR); such based amino acid composition (referred to as "BCAAem" in the instant disclosure) has been shown to lead an increased mitochondrial biogenesis both in cardiac and skeletal muscles (D'Antona et al., 2010). These effects were mediated by expression of endothelial nitric oxide synthase (eNOS) and consequent nitric oxide (NO) production (D'Antona et al., 2010).

The Inventor of the instant application surprisingly found that by adding specific acids to a composition comprising a similar combination of leucine, isoleucine, valine, threonine and lysine a significant increase in cell mitochondrial function, and thus in energy expenditure (EE), may be achieved.

The Inventor of the instant application tested a number of compositions different in terms of acids contained therein and found that compositions comprising as active agent a combination of citric acid, succinic acid and malic acid with leucine, isoleucine, valine, threonine and lysine are very effective for the indicated purposes. Indeed, compositions comprising the above stated active agent as well as compositions comprising the above stated active agent including further specific amino acids (listed in Table 1 below) are significantly more effective than the previously tested amino acids based composition (BCAAm) in promoting mitochondrial biogenesis and function.

The compositions were tested on Cardiac Muscle Cell Line (HL-1), i.e. cells representing an in vitro model of the cardiac functionality. Results deriving from analysis of these cardiomyocytes may be used to verify the efficacy of new compositions in the prevention of the heart failure.

In addition, the compositions herein disclosed were tested on immortalized brown adipocytes, an in vitro model of brown fat. A recent discovery has been shown the occurrence of Brown Adipose Tissue (BAT) in humans (Trayhurn, 2016).

Contrary to white adipose tissue (WAT), which is mainly an energy storing organ in the form of fat (triglycerides), brown adipose tissue (BAT) utilizes energy from food to produce heat (thermogenesis), therefore enhancing energy expenditure (EE).

This process is activated in response to both environmental (i.e. cold exposure) and nutritional (diet) cues, by means of increased expression and activity of the uncoupling protein 1 (UCP1; Cannon and Nedergaard, 2004).

The data provided in the instant application show the effectiveness of the compositions disclosed herein in the increase of UCP1 expression thus confirming their usefulness in medicine, in particular in the treatment of obesity and related disorders, such as for example insulin resistance and type 2 diabetes.

In one or more embodiments, the composition herein disclosed comprises an active agent, said active agent containing citric acid, succinic acid and malic acid in combination with leucine, isoleucine, valine, threonine, lysine, wherein the weight ratio between the total amount of citric acid, succinic acid and malic acid and the total amount of the amino acids leucine, isoleucine, valine, threonine, lysine is comprised between 0.05 and 0.3, preferably between 0.1 and 0.25.

In one or more embodiments, the active agent may further comprise one or more amino acids selected in the group consisting of histidine, phenylalanine, methionine, tryptophan, cysteine, tyrosine.

In a further embodiment, the active agent of the composition herein disclosed may also include aspartic acid and/or ornithine L-alpha ketoglutarate (OKG).

According to an embodiment, the composition comprises an active agent, the active agent consisting of leucine, isoleucine, valine, threonine, lysine, histidine, phenylalanine, methionine, tryptophan, cysteine and optionally tyrosine, as well as citric acid, succinic acid and malic acid, said amino acids being the sole amino acids contained in the composition.

In a further embodiment, the composition may comprise the amino acids isoleucine, leucine and valine in an amount between 35% and 65% by weight, preferably between 42% and 56% by weight with respect to the active agent weight.

In one or more embodiments, the weight ratio between leucine and citric acid is comprised between 5 and 1, preferably between 2.5 and 3.5.

In a further embodiment, the weight or molar amount of citric acid is higher than the weight or molar amount of each of malic acid and succinic acid. Preferably, the weight or molar amount of citric acid is higher than the weight or molar overall amount of malic acid plus succinic acid. In a further embodiment, the weight ratio between citric acid and the sum of malic acid and succinic acid is comprised between 1.0 and 4.0, preferably between 1.5 and 2.5. In a preferred embodiment, the citric acid:malic acid:succinic acid weight ratio is comprised between 10:1:1 and 2:1.5:1.5, preferably between 7:1:1 and 1.5:1:1, more preferably between 5:1:1 and 3:1:1.

According to some embodiments of the present disclosure, the preferred isoleucine:leucine molar ratio is comprised in the range 0.2-0.7, preferably in the range 0.30-0.60 and/or the preferred valine:leucine weight ratio is comprised in the range 0.2-0.70, preferably in the range 0.30-0.65.

In a further embodiment, the threonine:leucine molar ratio is comprised in the range of 0.10-0.90, preferably in the range 0.20-0.70 and/or the lysine:leucine weight ratio is comprised in the range of 0.20-1.00, preferably in the range 0.40-0.90.

In a preferred embodiment, the ratio between the overall molar amount of citric acid, malic acid, succinic acid and the overall molar amount of methionine, phenylalanine, histidine and tryptophan is higher than 1.35.

In one or more embodiments, the weight ratio between the sum of citric acid, malic acid, succinic acid and the sum of the branched chain amino acids leucine, isoleucine, valine is comprised between 0.1 and 0.4, preferably between 0.15 and 0.35.

In a further embodiment, the overall weight amount of the branched chain amino acids leucine, isoleucine, valine plus threonine and lysine is higher than the overall weight amount of the three acids (citric acid, malic acid, succinic acid). Preferably, the weight amount of the single acids (citric acid, succinic acid or malic acid) is less than the weight amount of each the single amino acids leucine, isoleucine, valine, threonine and lysine.

In a preferred embodiment, the weight ratio between the sum of citric acid, malic acid, succinic acid and the sum of the branched chain amino acids leucine, isoleucine, valine plus lysine and threonine is comprised between 0.05 and 0.30, preferably between 0.10 and 0.25.

In a further embodiment, the overall molar amount of lysine and threonine is higher than the overall molar amount of the three acids citric acid, succinic acid, malic acid. Preferably, the ratio between the overall molar amount of the three acids citric acid, succinic acid, malic acid and the overall molar amount of lysine and threonine is comprised between 0.10 and 0.70, preferably between 0.15 and 0.55.

In one or more embodiments, the composition herein disclosed further comprises vitamins, preferably selected in the group of vitamins B, such as vitamin $B_1$ and/or vitamin $B_6$.

In a further embodiment of the present disclosure, the composition may include carbohydrates, additives and/or flavouring substances.

Furthermore, in particular when preparing the compositions according to the instant disclosure, and specifically the active agent, the amino acid arginine is preferably avoided.

In addition, further amino acids preferably excluded by the composition herein disclosed are serine, proline, alanine.

Such amino acids can be counterproductive or even harmful in some concentrations or stoichiometric ratios within the composition.

The amino acids disclosed in the instant description can be replaced by respective pharmaceutically acceptable derivatives, namely salts.

As will emerge clearly hereinafter, the administration of the compositions according to the present disclosure is particularly effective in promoting mitochondrial biogenesis and mitochondrial function.

In a preferred embodiment, the disclosed compositions may be used in the treatment and/or prevention of a mitochondrial dysfunction-related disease, wherein said disease is obesity.

In a further embodiment, the disclosed compositions may be used in the treatment and/or prevention of a mitochondrial dysfunction-related disease, wherein said disease is an obesity-related disease, preferably selected between insulin resistance and type 2 diabetes.

According to a further embodiment, the amino acid compositions may comprise pharmaceutically acceptable excipients, like for example proteins, vitamins, carbohydrates, natural and artificial sweeteners and/or flavoring substances. In a preferred embodiment, the pharmaceutically acceptable excipients may be selected from whey proteins, maltodextrins, fructose, calcium caseinate, fish oil, citric acid or salts thereof, sucralose, sucrose esters, vitamin D3, group B vitamins.

For oral use, the compositions according to the description may be in the form of tablets, capsules, granules, gel, gelable powder, powder.

Further specifications, in terms of amounts and ratios among the various amino acids provided for by the compositions are contained in the attached claims, which form an integral part of the technical teaching provided herein in relation to the invention.

EXAMPLES

Table 1 shows different amino acid based compositions tested on HL-1 cells and on immortalized brown adipocytes as disclosed below.

Specifically, the BCAAem composition is the composition disclosed in EP 2 196 203 B1.

The composition named "B2" has as active agent a combination of amino acids similar to that of the BCAAem composition but further including citric acid. Such a composition also comprises vitamins B1 and B6.

The compositions named alpha 5 (α5), alpha 6 (α6), alpha 7 (α7) comprise an active agent containing amino acids and citric acid, succinic acid and malic acid. In addition, the alpha 7 composition's active agent also comprises OKG (ornithine L-α ketoglutarate) and the amino acid aspartate (Acid L-aspartic).

TABLE 1

| Compositions (%) | BCAAem | B2 | α5 | α6 | α7 |
|---|---|---|---|---|---|
| L-Leucine | 30.01 | 25.9555 | 31.0885 | 22.4500 | 21.7188 |
| L-Lysine HCl chlorhydrate | 19.58 | 16.9346 | 16.903 | 21.1300 | 20.4380 |
| L-Isoleucine | 15 | 12.9778 | 10.3628 | 11.2300 | 10.8594 |
| L-Valine | 15 | 12.9778 | 10.3628 | 11.2300 | 10.8594 |
| L-Threonine | 8.4 | 7.2675 | 7.254 | 13.1000 | 12.6693 |
| L-Cysteine | 3.6 | 3.1147 | 3.1089 | 2.8100 | 2.7149 |
| L-Histidine | 3.6 | 3.1147 | 3.1089 | 2.8100 | 2.7149 |
| L-Phenylalanine | 2.4 | 2.0764 | 2.0726 | 1.8700 | 1.8099 |
| L-Methionine | 1.2 | 1.0382 | 1.0363 | 0.9400 | 0.9050 |
| L-Tyrosine | 0.72 | 0.6229 | 0.6218 | — | — |
| L-Tryptophan | 0.48 | 0.4153 | 2.0726 | 0.9400 | 0.9050 |
| OKG (ornithine L-α ketoglutarate) | — | — | — | — | 0.9050 |
| Vitamin B1 (thiamine chlorhydrate) | — | 0.004 | 0.004 | 0.0200 | 0.0163 |
| Vitamin B6 (piridoxine chlorhydrate) | — | 0.0038 | 0.0038 | 0.0200 | 0.0186 |
| Citric acid anhydrous | — | 13.4969 | 8.0001 | 7.6500 | 7.4025 |
| Malic acid | — | — | 2.0000 | 1.9200 | 1.8551 |
| Acid L-aspartic | — | — | — | — | 2.3529 |
| Succinic acid | — | — | 2.0000 | 1.9200 | 1.8551 |
| Ratio Leucine:Isoleucine:Valine | 2:1:1 | 2:1:1 | 3:1:1 | 2:1:1 | 2:1:1 |

The compositions of Table 1 above may be prepared first by sifting all the components with a 0.8 mesh. To obtain a pre-mixture, each ingredient (in an amount <10% by weight of the total amount) is put in a polyethylene bag together with a portion of L-lysine HCl so as to obtain 10% of the weight of the total composition. The bag is then manually shaken for 5 minutes. The pre-mixture is then loaded in a mixer (Planetaria) together with the remainder of the ingredients and mixed for a period of 15 minutes at 120 rpm to obtain a homogeneous final composition.

The compositions listed in Table 1 have been administered to HL-1 cardiomyocytes and to immortalized brown adipocytes and the mitochondrial function has been evaluated as disclosed hereinafter.

Methods
Cells and Treatments
HL-1 Cardiomyocytes

HL-1 cardiomyocytes (a gift from W. C. Claycomb, New Orleans, School of Medicine) were plated in fibronectin/gelatin-coated flasks, grown to 70%-80% confluence in Claycomb medium (JRH Biosciences) supplemented with 100 μM norepinephrine (from a 10 mM norepinephrine [Sigma-Aldrich] stock solution dissolved in 30 mM L-ascorbic acid [Sigma-Aldrich]), 2 mM L-glutamine, 100 U/ml penicillin, 100 μg/ml streptomycin and 10% FBS (JRH Biosciences) as disclosed in Claycomb et al., 1998.

Cells were treated with 1% (w/v) of the compositions (dissolved in the Claycomb medium) shown in Table 1 for 24 hr or 48 hr.

At the end of these periods, mRNA and DNA were extracted from the cells or the cells were used to evaluate the oxygen consumption. Control cells were treated with Claycomb medium only.

Immortalized Brown Adipocytes

Immortalized brown adipocytes were purchased from Prof. Patrick Seale (University of Pennsylvania, Philadelphia, USA).

These are a SV40 immortalized BAT-derived cell line which, upon appropriate stimulation protocol, are able to differentiate in mature brown adipocytes.

Cells were routinely maintained in F12/DMEM (Gibco by Life technologies) with 10% FBS; for differentiation, confluent cells were treated with medium containing 10% FBS plus 0.5 mM isobutylmethylxanthine, 125 nM indomethacin, 1 μM dexamethasone, 20 nM insulin, 1 nM T3.

After 48 hr, cells switched to medium containing 10% FBS, 20 nM insulin, and 1 nM T3.

Preliminary experiments confirmed that 6-7 days of incubation with this medium are sufficient to induce the expression of UCP1 and other brown adipocyte markers. In particular, expression of PRDM16, a 140 kDa PR (PRD1-BF1-RIZ1 homologous)-domain-containing protein that is a marker of brown adipocyte differentiation (Seale et al., 2007) was increased in differentiated cells Therefore, after 6 days, cells were treated with 1% (w/v) different compositions shown in Table 1 (BCAAem, B2, α5) dissolved in F12/DMEM. Control cells were fed with medium only. Then, after 48 hours, cells were harvested and RNA was extracted for gene expression analysis.

Gene Expression and Mitochondrial Biogenesis Methods

Total RNA was isolated from HL-1 cardiomyocytes and from immortalized brown adipocytes using the RNeasy Mini Kit (Qiagen); one microgram of total RNA was reverse transcribed in cDNA using the iScript cDNA Synthesis Kit (Bio-Rad Laboratories) as described in D'Antona et al. (2010).

The gene relative level was calculated as $2^{-DDCT}$, in which DDCT corresponded to the difference between the DCT of either treatment and the DCT of the untreated group using GAPDH as internal control. The Delta-Delta-CT (DDCT) algorithm is an approximation method to determine relative gene expression with quantitative real-time PCR (qRT-PCR) experiments (see Livak and Schmittgen, 2001).

Primers (sequence reported in Table 2 below) were designed using Beacon Designer 2.6 software (Premier Biosoft International). Values were normalized with the expression of Glyceraldehyde 3-phosphate dehydrogenase (GAPDH).

TABLE 2

| Gene | Primer | Sequence | SEQ ID. | $T_a$ |
|---|---|---|---|---|
| GAPDH | Sense 5'-3' | AACTTTGGCATTGTGGAAGG | No. 1 | 60 |
|  | Antisense 5'-3' | ACACATTGGGGGTAGGAACA | No. 2 |  |
| Cyt c | Sense 5'-3' | ATAGGGGCATGTCACCTCAAAC | No. 3 | 61 |
|  | Antisense 5'-3' | GTGGTTAGCCATGACCTGAAAG | No. 4 |  |
| PGC-1α | Sense 5'-3' | ACTATGAATCAAGCCACTACAGAC | No. 5 | 61 |
|  | Antisense 5'-3' | TTCATCCCTCTTGAGCCTTTCG | No. 6 |  |
| Tfam | Sense 5'-3' | AAGACCTCGTTCAGCATATAACATT | No. 7 | 60 |
|  | Antisense 5'-3' | TTTTCCAAGCCTCATTTACAAGC | No. 8 |  |

TABLE 2-continued

| Gene | Primer | Sequence | SEQ ID. | $T_a$ |
|---|---|---|---|---|
| KFL15 | Sense 5'-3' | ACACCAAGAGCAGCCACCTCA | No. 9 | 60 |
|  | Antisense 5'-3' | TGAGATCGCCGGTGCCTTGA | No. 10 |  |
| PP2CM | Sense 5'-3' | ACCACAGGCAGGCGACTC | No. 11 | 60 |
|  | Antisense 5'-3' | TGGCTCATCAATGCGGTTATCC | No. 12 |  |
| mtDNA (12SrRNA) | Sense 5'-3' | ACATGCAAACCTCCATAGACCGG | No. 13 | 63 |
|  | Antisense 5'-3' | TCACTGCTGAGTCCCGTGGG | No. 14 |  |
| gDNA (GAPDH) | Sense 5'-3' | GGTCGCGGTGTGGGCATTTG | No. 15 | 60 |
|  | Antisense 5'-3' | CGTGATCGTAGCGTCTGGTT | No. 16 |  |

$T_a$ temperature of annealing (° C.); Accession number GAPDH: NM_008084.3; Accession number Cyt c: NM_007808; Accession number PGC-1α: AF049330; Accession number Tfam: NM_009360.4; Accession number KFL15: NM_023184.4; Accession number PP2CM: NM_175523.4; Mus musculus Mitochondrial, complete genome: NC_005089.1; gDNA (GAPDH): NC_000072.6; Primers code for 12S mitochondrial rRNA (NC_005098.1). GAPDH was used to normalize mitochondrial DNA.

For mitochondrial DNA (mtDNA) analysis, total DNA was extracted with QIAamp DNA extraction kit (QIAGEN).

mtDNA was amplified using primers specific for the mitochondrial DNA (mtDNA) gene and normalized to genomic DNA by amplification of GAPDH gene DNA. Primers, designed using Beacon Designer 2.6 software (Premier Biosoft International; Palo Alto, Calif.) are shown in Table 2 for gDNA.

Statistical Analysis

For all gene expression data, two-sided paired-sample t tests were used to compare values between control and treated cells. A p value<0.05 was considered statistically significant.

Oxygen Consumption

An amount of 1 ml of HL-1 cardiomyocytes treated with the compositions shown in Table 1 was re-suspended in Hank's balanced salt solution (Sigma) and spun down to pellet cells. A number of HL-1 cells was also supplemented with a nitic oxide (NO) donor, specifically with diethylen-etriamine-NO also called DETA-NO (Sigma-Aldrich, Milan, Italy), as positive control.

Then, cells were re-suspended in a respiration buffer (0.3 M mannitol, 10 mM KCl, 5 mM MgCl2, 10 mM K2PO4, pH 7.4) at a density of $3.0 \times 10^6$/ml.

Samples were analyzed at 37° C. in a gas-tight vessel equipped with a Clark-type oxygen electrode (Rank Brothers Ltd.) connected to a chart recorder.

The oxygen electrode was calibrated assuming the concentration of oxygen in the incubation medium as 200 µmol/l at 37° C.

Oxygen consumption was assessed with continuous mixing for about ten minutes. The slope of the trace recorder was then used to calculate oxygen consumption. Oxygen content may vary depending on the amount of cells. Thus, protein content, which directly correlates with cell content, has been used to normalize the oxygen consumption in cell samples. Protein content was determined by using the bicinchoninic acid protein (BCA) assay.

Results

HL-1 Cardiomyocytes Mitochondrial DNA (mtDNA)

The mitochondrial DNA (mtDNA) was first evaluated in the cells treated with the different amino acids compositions in order to verify their effects on mitochondrial mass.

As shown in FIG. 1, HL-1 cardiomyocytes treated with α5 composition showed the most significant increase in mtDNA with respect to the mtDNA evaluated in control cells (CT), in B2-treated cells and, very interestingly, in cells treated with the BCAAem composition.

HL-1 Cardiomyocytes PGC-1α, Tfam and Cyt c

The effect of the different amino acid compositions was also tested on mitochondrial biogenesis. Specifically, the expression by HL-1 cardiomyocytes of the following markers was evaluated:

peroxisome proliferator-activated receptor gamma coactivator 1-alpha (PGC-1α), the master regulator of mitochondrial biogenesis, mitochondrial DNA transcription factor A (Tfam), the mtDNA transcription factor regulating mtDNA replication, cytochrome complex (Cyt c), the respiratory complex protein.

Comparison between the results obtained following the administration of the BCAAem composition, the B2 composition (i.e. the composition similar to the BCAAem composition but also comprising citric acid), α5 (i.e. the composition comprising as active agent other than amino acids also the acids citric acid, succinic acid, malic acid) showed that the α5 composition was the most effective in promoting the expression of the above markers in HL-1 cardiomyocytes cells.

Moreover, a time-course effect was observed: after a supplementation of 48 hr with the α5 composition comprising amino acids listed in Table 1 together with the three carboxylic acids indeed the increase was still more pronounced over the basal values.

Figure 2:
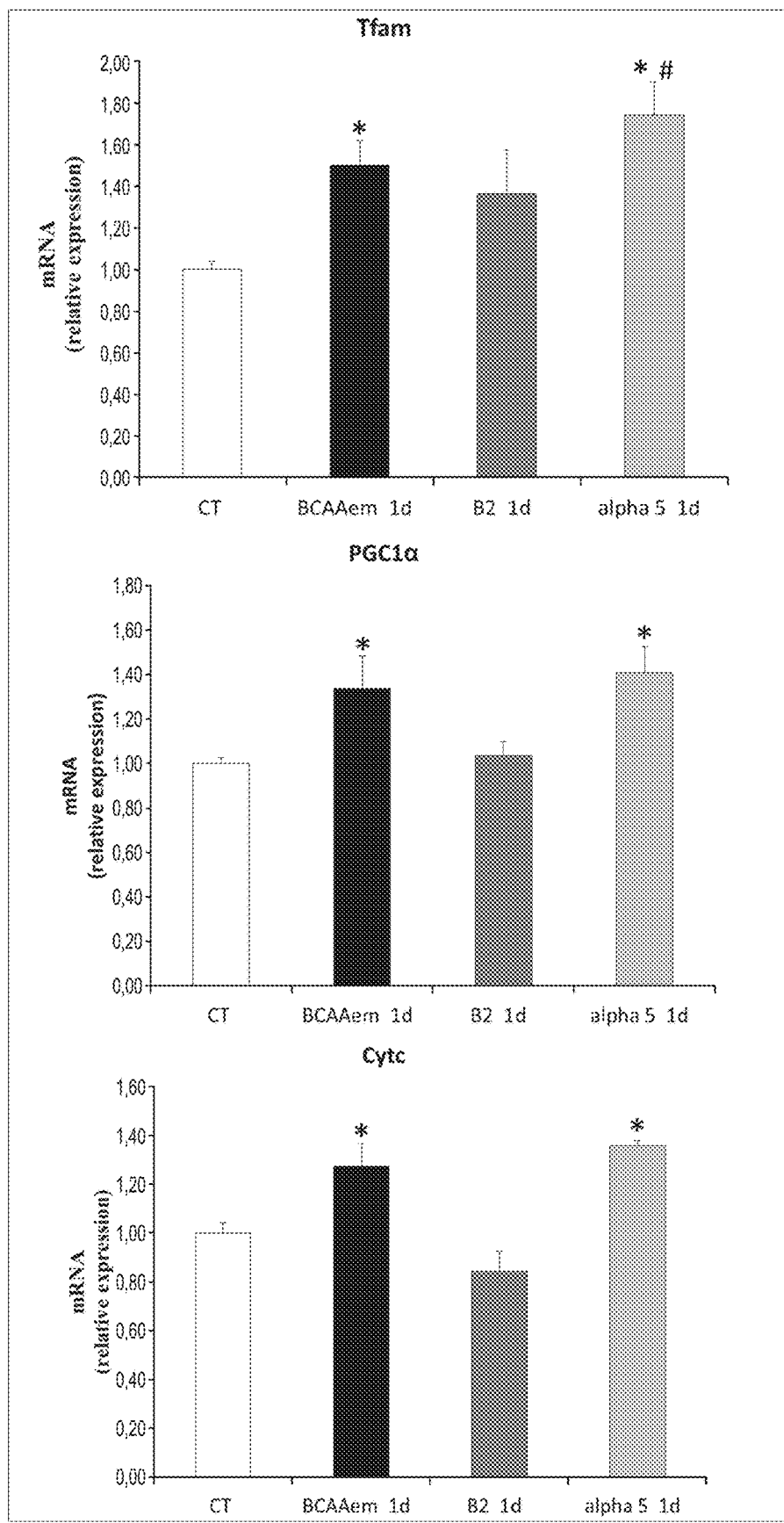
FIG. 2 shows the mRNA levels of mitochondrial biogenesis marker (Tfam, PGC-1α, Cyt c) levels analysed by means of quantitative PCR in HL-1 cardiomyocytes treated with amino acid based compositions for 24 hr (1 d). Quantitative PCR is performed in triplicate and normalized to GAPDH (n=3, mean±SEM). *p<0.05 vs. untreated cells, expressed as 1.0. #p<0.05 vs. BCAAem.
Figure 3:
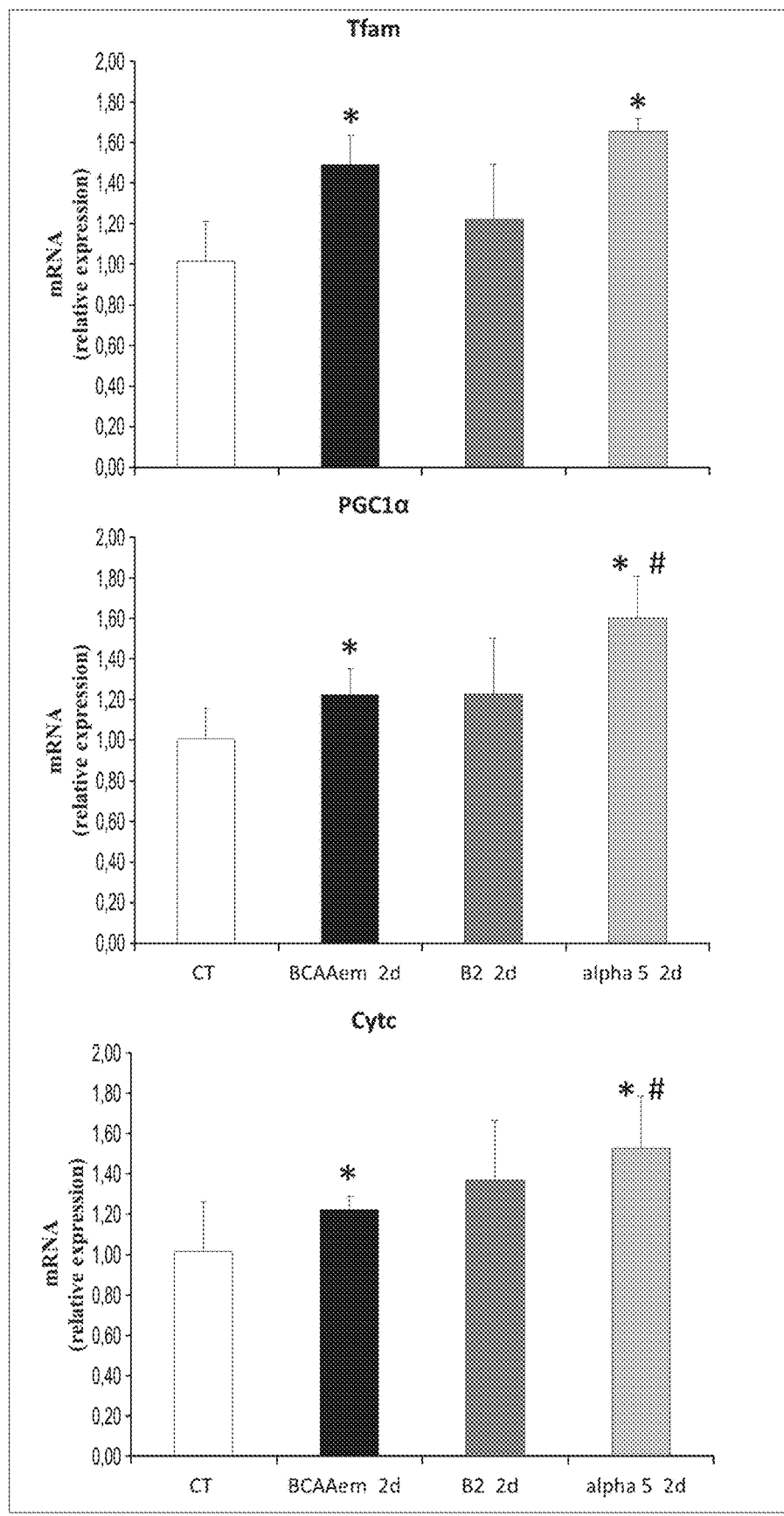
FIG. 3 shows the mRNA levels of mitochondrial mitochondrial biogenesis marker (Tfam, PGC-1α, Cyt c) analysed by quantitative PCR in HL-1 cardiomyocytes treated with amino acid based compositions for 48 hr (2 d). Quantitative PCR is performed in triplicate and normalized to GAPDH (n=3, mean±SEM). *p<0.05 vs. untreated cells, expressed as 1.0. #p<0.05 vs. BCAAem.

The increase was also statistically significant with respect to the value of the BCAAem composition for Tfam when compared to 24 hr treatment (FIG. 2) and for PGC-1α and for Cyt c after 48 hr treatment (FIG. 3).

HL-1 Cardiomyocytes KFL15 and PP2CM

Krüppel-like factor 15 (KFL15) and mitochondrial matrix-targeted protein phosphatase 2C family member (PP2CM) are proteins that regulate the catabolism of the branched chain amino acids (BCAA).

The first steps in BCAA catabolism are common to the three BCAAs and require the mitochondrial enzymes BCAA aminotransferase (BCAT) and branched-chain α-keto acid dehydrogenase complex (BCKDC).

In the first and fully reversible step of degradation, mitochondrial BCAT transfers the amino group from BCAAs to α-ketoglutarate to form the corresponding branched-chain α-keto acids (BCKAs) and glutamate.

Thereafter, BCKDC catalyses decarboxylation of the carboxyl groups of BCKAs, to form the corresponding branched-chain acyl-CoA esters.

This reaction is irreversible and, therefore, commits the BCAAs to degradation.

BCKDC activity is regulated by end-product allosteric inhibition by NADH, α-ketoisocaproate, and branched-chain acyl-CoA esters.

BCKDC activity is determined by the phosphorylation status of its regulatory subunit E1a.

When the BCAA level is low, E1a is hyper-phosphorylated by a BCKD kinase, leading to inhibition of BCKDC activity and preservation of free BCAA.

When the BCAA level is high, E1a is dephosphorylated by a mitochondrial-targeted 2C-type Ser/Thr protein phosphatase named PP2C in mitochondria (PP2CM) or protein phosphatase, Mg2+/Mn2+ dependent 1K (PPM1K), leading to BCKDC activation and reducing total BCAAs (Bifari and Nisoli, 2016).

In addition, KLF15 was found to increase BCAT, BCKDC, and PP2CM gene expression in heart (Sun et al., 2016).

Figure 4:
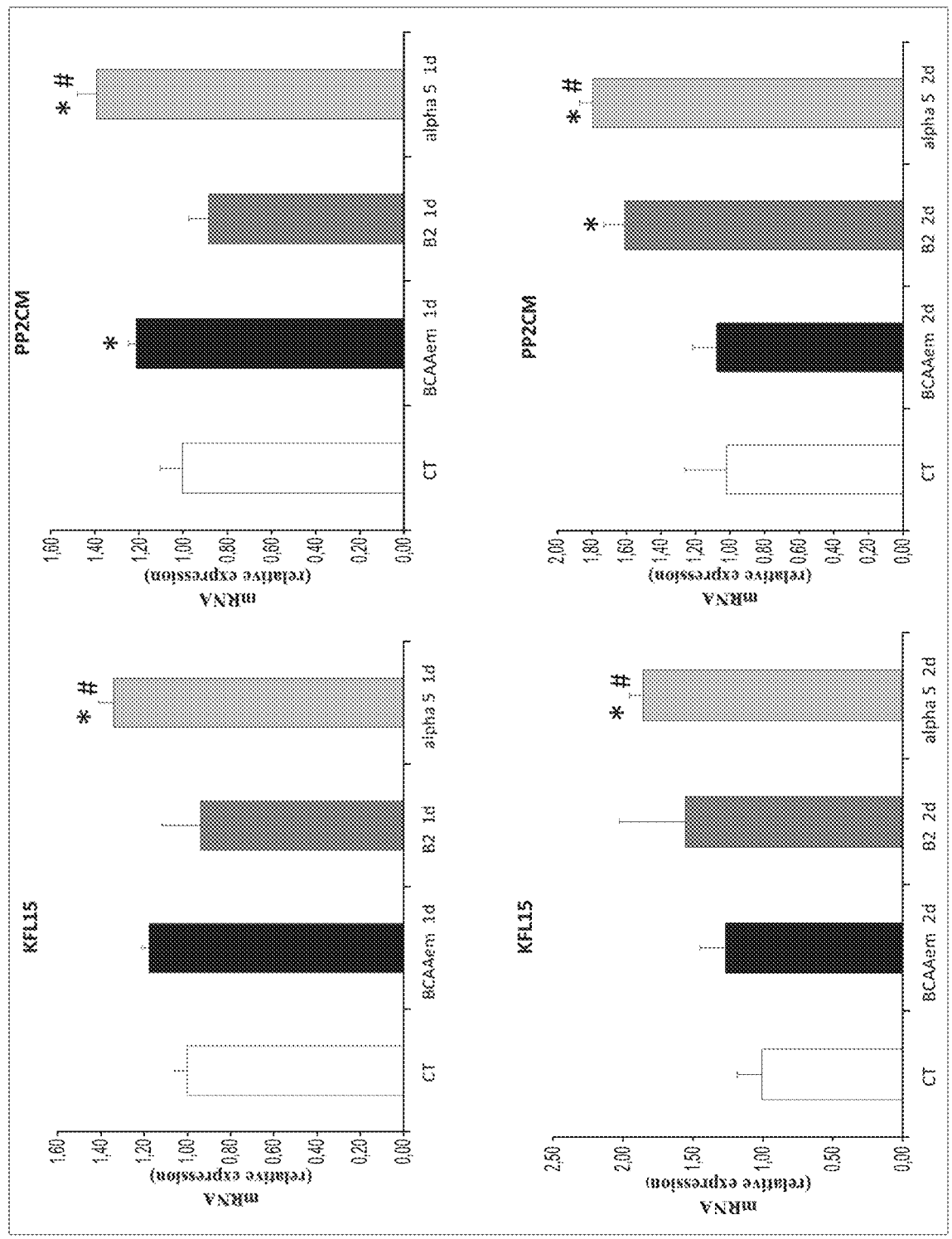
FIG. 4 shows the mRNA levels of Krüppel-like factor 15 (KFL15) and mitochondrial matrix-targeted protein phosphatase 2C family member (PP2CM) which are proteins regulating the catabolism of the branched chain amino acids (BCAA). PP2CM and KFL15 have been analysed by quantitative PCR in HL-1 cardiomyocytes treated with amino acid based compositions for 24 hr (1 d) or 48 hr (2 d). Quantitative PCR is performed in triplicate and normalized to GAPDH (n=3, mean±SEM). *p<0.05 vs. untreated cells, expressed as 1.0; #p<0.05 vs. BCAAem and B2.

The evaluation of the mRNA levels of PP2Cm and KFL13 showed that α5 composition increased PP2CM and KLF15 mRNA levels over the basal value in HL-1 cardiomyocytes. The increase was significant even over BCAAem composition (FIG. 4)

These results shows that compositions comprising an active agent, the active agent containing leucine, isoleucine, valine, threonine, lysine and citric acid, succinic acid and malic acid, are very effective in promoting mitochondrial function and activate more efficiently mitochondrial biogenesis even with respect to the BCAAem composition in metabolically active cells.

HL-1 Cardiomyocytes Oxygen Consumption (OCR)

Oxygen consumption of HL-1 cells supplemented with different compositions was tested. Cells supplemented with diethylenetriamine-NO (DETA-NO) as positive control were also tested. The effect of DETA-NO on increasing the cell oxygen consumption has been shown (Nisoli et al., 2003). NO was found to trigger mitochondrial biogenesis in cells as diverse as brown adipocytes and 3T3-L1, U937, and HeLa cells. This effect of nitric oxide was dependent on cyclic guanosine 3',5'-monophosphate (cGMP) and was mediated by the induction of PGC-1α, a master regulator of mitochondrial biogenesis (Nisoli et al., 2003).

After 48 h of DETA-NO treatment, a rise of oxygen consumption was observed, as expected.

Figure 5:
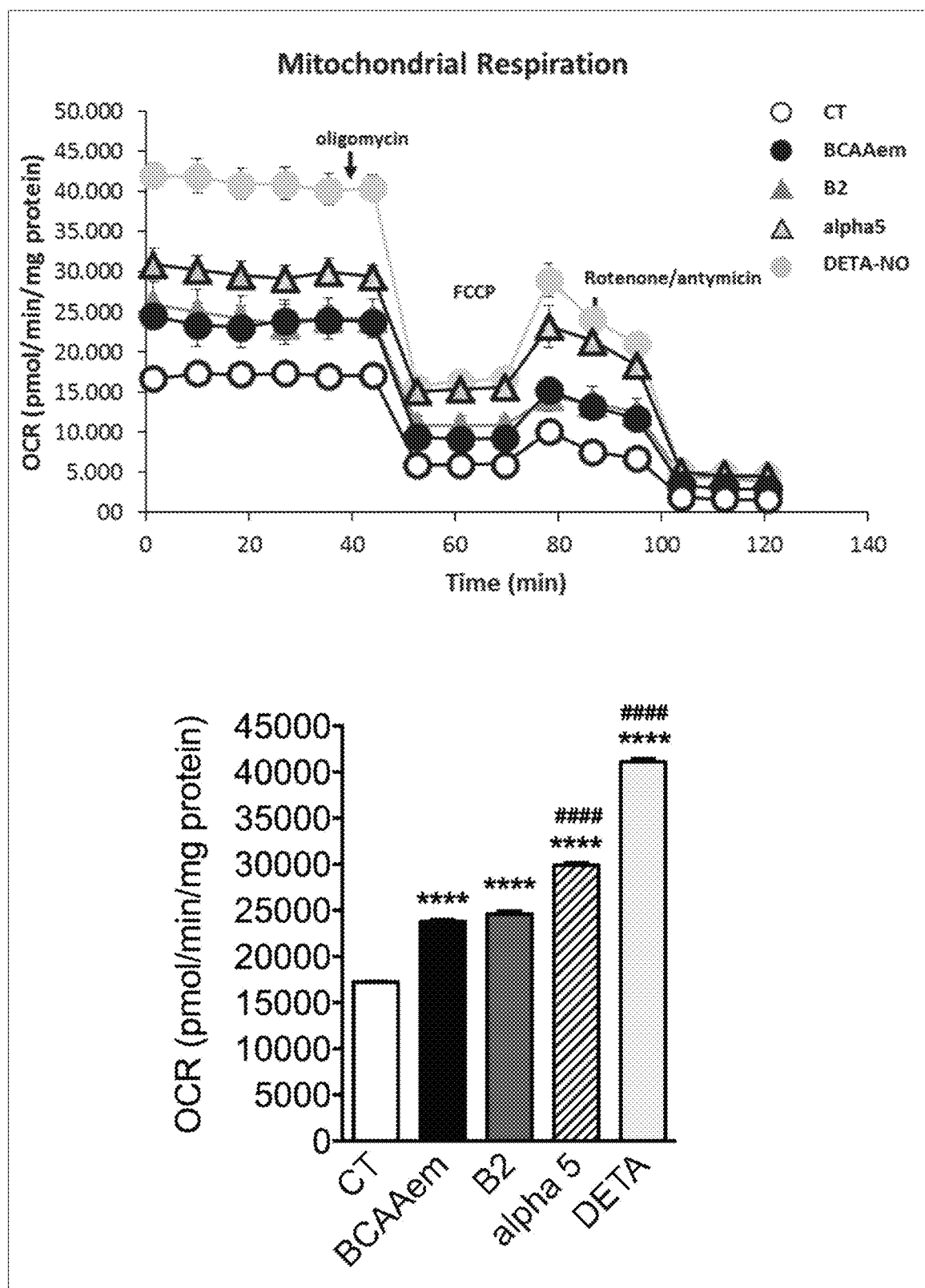
FIG. 5 shows an evaluation of the oxygen consumption rate (OCR). Oxygen consumption in HL-1 cardiomyocytes treated with amino acid based compositions or DETA-NO for 48 hr. ****p<0.001 vs. untreated cell; ####p<0.001 vs. BCAAem and B2.

Most notably, a markedly increase in oxygen consumption was observed when HL-1 cells were supplemented with α5 composition for 48 hr thus indicating a rise in mitochondrial activity (FIG. 5).

The increase is significantly higher than that observed after B2 and BCAAem compositions administration.

UCP1 Expression in Immortalized Brown Adipocytes

Figure 6:
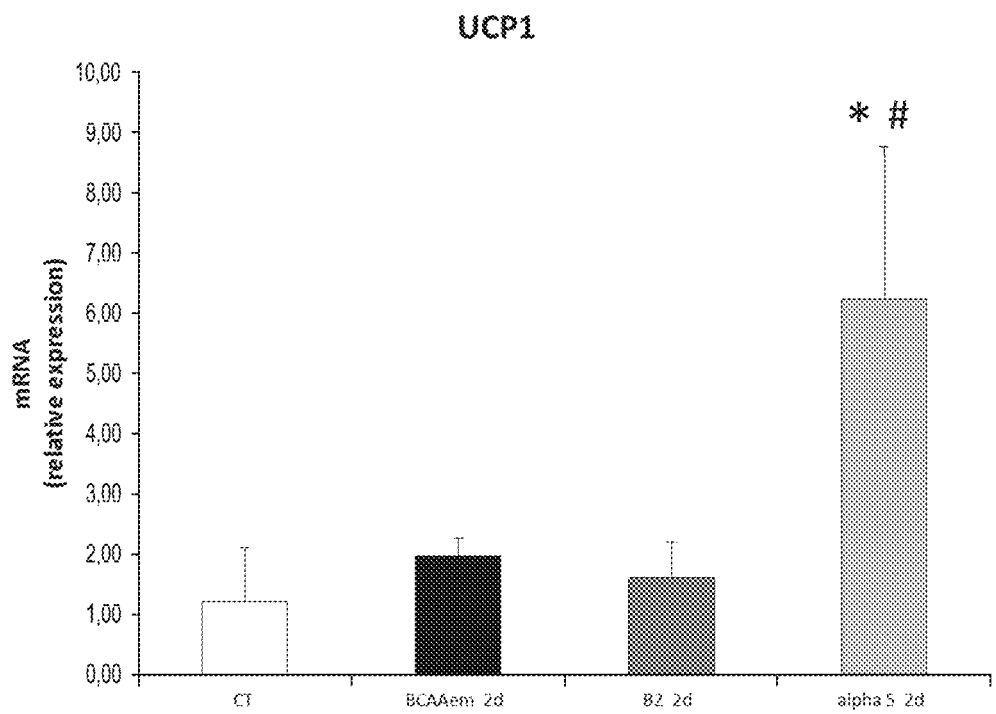
FIG. 6 shows UCP1 expression in immortalized brown adipocytes (Seale et al., 2007) after 48 hr (2 d) treatment. CT: untreated, control cells. Value of untreated cells (CT) is taken as 1.0. * significant vs. CT. # significant vs. BCAAem; RT-PCR is performed in triplicate and normalized to GAPDH (n=3, mean±SEM).

As shown in FIG. 6, 48 hours treatment with the disclosed compositions increased, albeit to different extents, UCP1 expression in immortalized brown adipocytes.

Among different mixtures, α5 was the most effective in inducing UCP1 expression with respect to untreated cells (p=0.04 vs CT); α5 also increased UCP1 mRNA more efficiently when compared to BCAAem mixture (p=0.05).

PGC-1α Expression in Immortalized Brown Adipocytes

Figure 7:
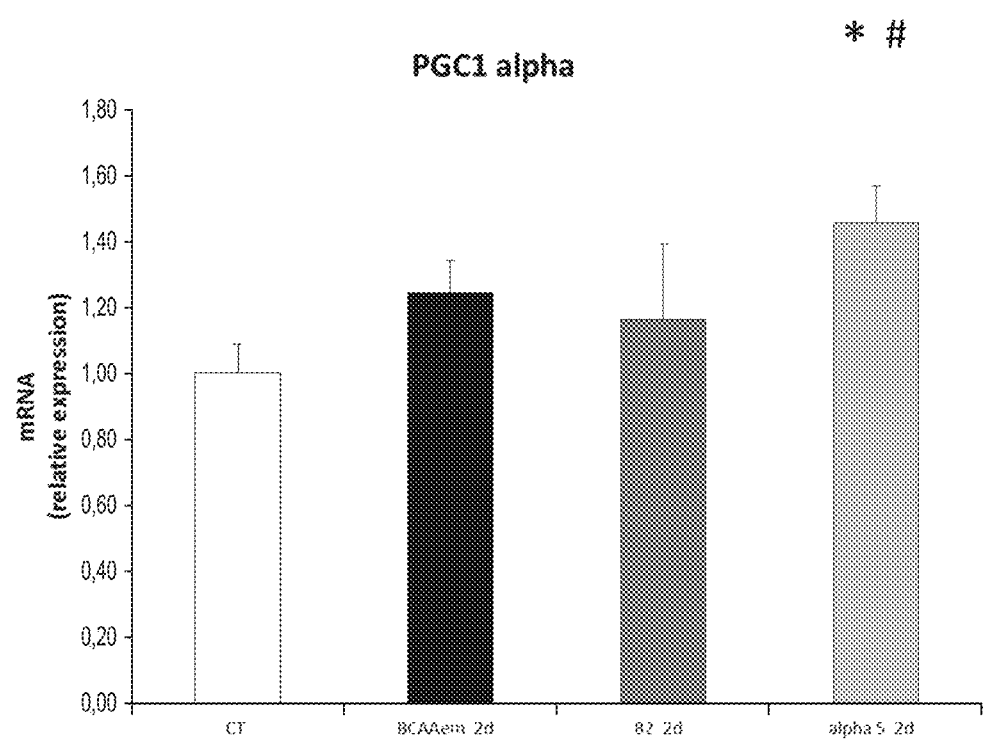
FIG. 7 shows PGC-1α expression in immortalized brown adipocytes after 48 hr (2 d) treatment. CT: untreated, control cells, Value of untreated cells (CT) is taken as 1.0. * significant vs. CT. # significant vs. BCAAem. PCR is performed in triplicate and normalized to GAPDH (n=3, mean±SEM).

In line with UCP1 data, α5 mixture also significantly increased expression of PGC-1α (p=0.01), thus confirming the capability of this composition in activating mitochondrial biogenesis (FIG. 7). Of note, α5 was also more effective than BCAAem composition in increasing PGC-1α expression.

Taken together, these results indicate that compositions comprising an active agent, the active agent containing a combination of leucine, isoleucine, valine, threonine, lysine, citric acid, succinic acid and malic acid is significantly more active in promoting mitochondrial biogenesis, mitochondrial function and BCAA catabolism.

The composition alpha 6 (α6) and alpha 7 (α7), providing for an active ingredient comprising the BCAAs, threonine and lysine, as well as citric acid, succinic acid and malic acid are believed to attain similar advantages.

Of note, catabolism of BCAA, which are enriched in the mixture, in addition to Acetyl-CoA, provides succinyl-CoA. This latter could activate succinyl-Coa synthetase reaction, which, in turn produces succinate as a substrate for the subsequent reaction of succinate dehydrogenase.

Providing succinate, along with BCAA, in the mixture could therefore also stimulate the succinate dehydrogenase reaction, thus further boosting the cycle. Of note, succinate dehydrogenase, by directly providing $FADH_2$, is also part of mitochondrial the electron transport chain (complex II). Its stimulation by succinate could therefore directly activate mitochondrial redox carriers and increase membrane potential, thus enhancing proton gradient, oxygen consumption and ATP synthesis.

At the same time, malate supplement could activate malate dehydrogenase reaction and increase NADH levels; this would also provide substrates for complex I and therefore increase ATP levels, in the same manner as succinate-derived $FADH_2$. On the other hand, malate could stimulate the activity of malate-aspartate shuttle. This would favour the entry of also cytosolic NADH into mitochondria, which would otherwise be impermeable through mitochondrial membrane, thus rendering it available for mitochondrial oxidation. This would further increase mitochondrial activity and oxygen consumption.

In addition, energy obtained from the breakdown of carbohydrates or fats is derived by the process of mitochondrial oxidative phosphorylation. Catabolism of glucose and fatty acids by TCA (tricarboxylic acid) cycle provides NADH and $FADH_2$ molecules. Electrons from NADH and $FADH_2$ are then transferred to molecular oxygen through protein complexes in the inner mitochondrial membrane and this process generated a proton gradient across the mitochondrial membrane. Protons re-entry into mitochondria through ATP synthase complex, which uses energy from the gradient to synthesize adenosine triphosphate (ATP). In this way, electron transport is coupled to ATP synthesis.

On the other hand, UCP1, a mitochondrial transmembrane protein which is activated in BAT after cold or excess nutrients, dissipates proton gradient across the mitochondrial inner membrane, and this results in the uncoupling of oxidative phosphorylation. Energy derived from proton gradient is no more available for ATP synthesis and, since UCP1 do not form ATP, energy from the proton gradient is therefore liberated as heat.

Increased mitochondrial biogenesis and number also underlies the thermogenic program which occurs in BAT in response to the above mentioned stimuli, and a key role in this process is played by Peroxisome proliferator-activated receptor gamma coactivator 1-alpha (PGC-1α), a cold-inducible transcriptional coactivator able to regulate the expression of both UCP1 and other factors involved in mitochondrial biogenesis (Scarpulla, 2011). Consequently, stimulation of UCP1 activity and heat production in BAT could be a potential therapeutic approach for reversing obesity, and there is great interest for searching agents and/or nutritional strategies that would stimulate the activity of this tissue.

It is also noteworthy that, more recently, a third type of fat, besides WAT and BAT, has been recognized in some WAT depots and has been described as beige or "brite" fat. In response to the same stimuli which induce thermogenesis in BAT, this tissue undergoes the process of "browning", by enhancing the expression of thermogenic proteins, such as UCP1, and by also inducing typical brown fat markers and, consequently, leading to an enhancement of energy expenditure (EE, Song et al., 2017). These findings, therefore, challenge the common view of WAT as a metabolically inert organ and strengthen the hypotheses of a more plastic and "druggable" target tissue, making thus brite fat another potential target for an anti-obesity therapeutic or nutritional approach.

Altogether, these results show that the compositions herein disclosed are able to increase mitochondrial biogenesis and function, BCAA catabolism in HL-1 cardiomyocytes and to promote brown adipocytes markers expression.

From the foregoing, it emerges clearly how the compositions according to the instant disclosure are useful for the treatment of pathological conditions distinguished by insufficient mitochondrial function in humans and in animals.

REFERENCES

Bifari F, Nisoli E. Branched-chain amino acids differently modulate catabolic or anabolic states in mammals: a pharmacological point of view. Br J Pharmacol. 2016 Sep. 17. doi: 10.1111/bph.13624. [Epub ahead of print].

Cannon B, Nedergaard J. Brown adipose tissue: function and physiological significance. Physiol Rev. 2004 January; 84(1):277-359. Review Claycomb W C, Lanson N A Jr, Stallworth B S, Egeland D B, Delcarpio J B, Bahinski A, Izzo N J Jr. HL-1 cells: a cardiac muscle cell line that contracts and retains phenotypic characteristics of the adult cardiomyocyte. Proc Natl Acad Sci USA 95: 2979-2984, 1998.

D'Antona G, Ragni M, Cardile A, Tedesco L, Dossena M, Bruttini F, Caliaro F, Corsetti G, Bottinelli R, Carruba M O, Valerio A, Nisoli E. Branched-chain amino acid supplementation promotes survival and supports cardiac and skeletal muscle mitochondrial biogenesis in middle-aged mice. Cell Metab. 12: 362-372, 2010.

Livak K J, Schmittgen T D. Analysis of relative gene expression data using real-time quantitative PCR and the 2(-Delta Delta C(T)) Method. Methods 25: 402-408, 2001.

Nisoli E, Clementi E, Paolucci C, Cozzi V, Tonello C, Sciorati C, Bracale R, Valerio A, Francolini M, Moncada S, Carruba M O. Mitochondrial biogenesis in mammals: the role of endogenous nitric oxide. Science: 299(5608):896-9, 2003.

Nisoli E, Tonello C, Cardile A, Cozzi V, Bracale R, Tedesco L, Falcone S, Valerio A, Cantoni O, Clementi E, Moncada S, Carruba M O. Calorie restriction promotes mitochondrial biogenesis by inducing the expression of eNOS. Science 310: 314-317, 2005.

Seale P, Kajimura S, Yang W, Chin S, Rohas L M, Uldry M, Tavernier G, Langin D,Spiegelman B M. Transcriptional control of brown fat determination by PRDM16. Cell Metab. 6: 38-54, 2007

Song N J et al. Induction of thermogenic adipocytes: molecular targets and thermogenic small molecules. Exp Mol Med. 2017 Jul. 7; 49(7):e353. doi: 10.1038/emm.2017.70. Review. PubMed PMID: 28684864.

Sun H, Olson K C, Gao C, Prosdocimo D A, Zhou M, Wang Z, Jeyaraj D, Youn J Y, Ren S, Liu Y, Rau C D, Shah S, Ilkayeva O, Gui W J, William N S, Wynn R M, Newgard C B, Cai H, Xiao X, Chuang D T, Schulze P C, Lynch C, Jain M K, Wang Y. Catabolic Defect of Branched-Chain Amino Acids Promotes Heart Failure. Circulation 133: 2038-2049, 2016.

Scarpulla R C. Metabolic control of mitochondrial biogenesis through the PGC-1 family regulatory network. Biochim Biophys Acta. 2011; 1813(7):1269-78

Trayhurn P. Recruiting Brown Adipose Tissue in Human Obesity. Diabetes. 2016; 65(5):1158-60.

Wells G D, Noseworthy M D, Hamilton J, Tarnopolski M, Tein I. Skeletal muscle metabolic dysfunction in obesity and metabolic syndrome. Can J Neurol Sci. 2008; 35 (1):31-40. Review World Health Organization. Obesity and overweight. WHO Media Centre.Updated August 2014. Available from http://www.who.int/mediacentre/factsheets/fs311/en/.

The invention claimed is:

1. A method of treatment for obesity, comprising administering to a subject in need thereof a therapeutically effective amount of a composition comprising an active agent, said active agent comprising leucine, isoleucine, valine, threonine, lysine, citric acid, succinic acid and malic acid,
   wherein the citric acid:malic acid:succinic acid weight ratio is between 10:1:1 and 1:3:1:1,
   wherein the composition comprises the amino acids isoleucine, leucine and valine in an amount by weight between 35% and 65%,
   wherein the weight ratio between (i) the sum of citric acid, malic acid and succinic acid and (ii) the sum of leucine, isoleucine and valine is between 0.1 and 0.4,
   wherein the weight ratio between (i) the sum of citric acid, malic acid and succinic acid and (ii) the sum of leucine, isoleucine, valine, lysine and threonine is between 0.05 and 0.3 and
   wherein the weight ratio between leucine and citric acid is comprised between 5 and 1.

2. The method of claim 1, wherein the weight ratio between citric acid and the sum of malic acid and succinic acid is between 1.0 and 4.0.

3. The method of claim 1, wherein the weight ratio between citric acid and the sum of malic acid and succinic acid is between 1.5 and 2.5.

4. The method of claim 1, wherein the citric acid:malic acid:succinic acid weight ratio is between 10:1:1 and 2:1.5:1.5.

5. The method of claim 1, wherein the citric acid:malic acid:succinic acid weight ratio is between 7:1:1 and 1.5:1:1.

6. The method of claim 1, wherein the citric acid:malic acid:succinic acid weight ratio is between 5:1:1 and 3:1:1.

7. The method of claim 1, wherein said active agent further comprises at least one amino acid selected from the group consisting of histidine, phenylalanine, methionine, tryptophan, tyrosine, and cysteine.

8. The method of claim 1, wherein said active agent further comprises histidine, phenylalanine, methionine, tryptophan and cysteine.

9. The method of claim 1, wherein said active agent further comprises histidine, phenylalanine, methionine, tryptophan, cysteine and tyrosine.

10. The method of claim 8, wherein the ratio between the overall molar amount of citric acid, malic acid and succinic acid, and the overall molar amount of methionine, phenylalanine, histidine and tryptophan is higher than 1.35.

11. The method of claim 1, wherein the ratio between the overall molar amount of citric acid, succinic acid and malic acid, and the overall molar amount of lysine and threonine is between 0.1 and 0.7.

12. The method of claim 1, wherein the ratio between the overall molar amount of citric acid, succinic acid and malic acid, and the overall molar amount of lysine and threonine is between 0.15 and 0.55.

13. The method of claim 1, wherein the weight or molar amount of citric acid is higher than the overall weight or molar amount of malic acid and succinic acid.

14. The method of claim 1, wherein the weight ratio between leucine and citric acid is between 2.50 and 3.50.

15. The method of claim 1, wherein said active agent is free of arginine.

16. The method of claim 1, wherein the composition further comprises one or more vitamins.

17. The method of claim 1, wherein the composition further comprises one or more vitamins selected from the group of vitamins B.

\* \* \* \* \*